United States Patent
Whitfield et al.

(10) Patent No.: US 12,274,797 B2
(45) Date of Patent: Apr. 15, 2025

(54) BIOERODIBLE DRUG DELIVERY IMPLANTS

(71) Applicant: HERA HEALTH SOLUTIONS INC., Frisco, TX (US)

(72) Inventors: Garrett Whitfield, Denver, NC (US); Idicula Mathew, Frisco, TX (US); Matthew Devlin, Summit, NJ (US); Anthony McVey, Huntsville, NC (US)

(73) Assignee: HERA HEALTH SOLUTIONS INC., Frisco, TX (US)

( * ) Notice: Subject to any disclaimer, the term of this patent is extended or adjusted under 35 U.S.C. 154(b) by 0 days.

(21) Appl. No.: 17/240,363

(22) Filed: Apr. 26, 2021

(65) Prior Publication Data

US 2021/0244678 A1 Aug. 12, 2021

Related U.S. Application Data

(63) Continuation of application No. 16/029,624, filed on Jul. 8, 2018, now abandoned.

(60) Provisional application No. 62/530,166, filed on Jul. 8, 2017.

(51) Int. Cl.
| | | |
|---|---|---|
| *A61K 9/70* | (2006.01) | |
| *A61K 31/57* | (2006.01) | |
| *A61K 47/34* | (2017.01) | |
| *D01D 5/00* | (2006.01) | |
| *D01D 7/00* | (2006.01) | |
| *D04H 1/728* | (2012.01) | |

(52) U.S. Cl.
CPC ............ *A61K 9/7007* (2013.01); *A61K 31/57* (2013.01); *A61K 47/34* (2013.01); *D01D 7/00* (2013.01); *D04H 1/728* (2013.01); *D01D 5/003* (2013.01); *D10B 2331/041* (2013.01); *D10B 2401/12* (2013.01); *D10B 2509/00* (2013.01)

(58) Field of Classification Search
CPC ...... A61K 9/7007; A61K 31/57; A61K 47/34; D01D 7/00; D01D 5/003; D04H 1/728; D10B 2331/041; D10B 2401/12; D10B 2509/00
See application file for complete search history.

(56) References Cited

U.S. PATENT DOCUMENTS

| | | | | |
|---|---|---|---|---|
| 6,306,428 B1 * | 10/2001 | Lehmann | ............. | A61K 9/2086 |
| | | | | 424/438 |
| 2004/0076661 A1 * | 4/2004 | Chu | ..................... | A61L 27/58 |
| | | | | 424/443 |
| 2010/0291182 A1 * | 11/2010 | Palasis | ................. | A61K 31/485 |
| | | | | 514/282 |
| 2011/0038936 A1 * | 2/2011 | Griswold | ............... | A61K 31/17 |
| | | | | 514/249 |
| 2011/0236462 A1 * | 9/2011 | Shaked | ................... | A61P 43/00 |
| | | | | 424/432 |
| 2014/0094407 A1 | 4/2014 | Ron et al. | | |
| 2015/0038415 A1 | 2/2015 | Zupancich | | |
| 2015/0142026 A1 | 5/2015 | Hoke | | |
| 2016/0325013 A1 * | 11/2016 | Li | ........................ | A61P 21/00 |

FOREIGN PATENT DOCUMENTS

| | | |
|---|---|---|
| CN | 1529653 A | 9/2004 |
| WO | 2005089814 A1 | 9/2005 |

OTHER PUBLICATIONS

International Search Report and Written Opinion issued in International Application No. PCT/US2018/041175, mailed Sep. 7, 2018.
Examination Report issued for Indian Application No. 202017003271, dated Apr. 23, 2021.
Communication Pursuant to Article 94(3) EPC, issued for Application No. EP18832426.3, dated Jan. 13, 2022.
Office Action for Brazilian Patent Application No. BR112020000320-4 dated Jun. 21, 2022.
Van Laarhoven J et al, "In vitro release properties of etonogestrel and ethinyl estradiol from a contraceptive vaginal ring", International Journal of Pharmaceutics, Elsevier, NL, vol. 232, No. 1-2, doi:10.1016/S0378-5173(01)00900-0, ISSN 0378-5173,(Jan. 31, 2002), pp. 163-173, (Jan. 31, 2002), XP027429886.
Office Action for Israeli Patent Application No. 271865 dated Aug. 23, 2022.
China Patent Office, Second Office Action and Search Report for CN Application No. 201880055600.4, issued Sept. 4, 2023, 24 pages.
China Patent Office, Decision of Final Rejection for CN Application No. 201880055600.4, issued Jan. 9, 2024, 20 pages.
Australia Patent Office, First Examination Report for AU Application No. 2018301320, issued Jun. 21, 2023, 5 pages.

* cited by examiner

*Primary Examiner* — Doan T Phan

(74) *Attorney, Agent, or Firm* — Meunier Carlin & Curfman LLC

(57) ABSTRACT

Disclosed herein are bioerodible drug delivery devices including one or more active agents, and related methods. The devices are useful for administering a wide variety of agents over prolonged periods of time.

3 Claims, 2 Drawing Sheets

BIOERODIBLE DRUG DELIVERY IMPLANTS

CROSS-REFERENCE TO RELATED APPLICATION

This application claims the benefit of U.S. Provisional Application 62/530,166, filed Jul. 8, 2017, the contents of which are hereby incorporated in its entirety.

FIELD OF THE INVENTION

The present invention relates, in some aspects, to implantable, bioerodible drug delivery devices and related methods. The devices are useful for administering any pharmaceutical agent over a prolonged period of time.

BACKGROUND

Many therapeutic drugs are used in chronic fashion, meaning a patient will take one or more dosage forms each and every day for prolonged and/or indefinite lengths of time. For some patients, physically swallowing one or more pills each and every day can be inconvenient or impractical. For certain psychiatric drugs, patient non-compliance can also present challenges for consistent dosing of the medicament. Implantable drug delivery devices can be implanted into a patient and gradually release one or more active substances for prolonged lengths of time. In many cases however, these devices are made from non-degradable materials and therefore must be surgically removed once the total drug content has been administered.

There remains a need for improved drug delivery devices for controlled administration of a wide variety of therapeutic drugs. There remains a need for improved drug delivery devices that are completely bioerodible, and therefore do not need to be removed at the conclusion of drug administration.

SUMMARY

Disclosed herein are implantable, bioerodible, drug delivery devices and related methods. The devices can be used to administer a wide variety of agents, and are particularly suitable for the prolonged delivery of drugs at a constant rate. As such, the devices are especially useful for the administration of contraceptives, hormone therapies, chemotherapeutics, and veterinary drugs, among others. The devices include electrospun fibers blended with one or more active agents to form a random sheet that is arranged in a rolled configuration in order to achieve the desired release and degradation rate.

The details of one or more embodiments are set forth in the descriptions below. Other features, objects, and advantages will be apparent from the description and from the claims.

DETAILED DESCRIPTION

Before the present devices and methods are disclosed and described, it is to be understood that the devices and methods are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Figure 1A:
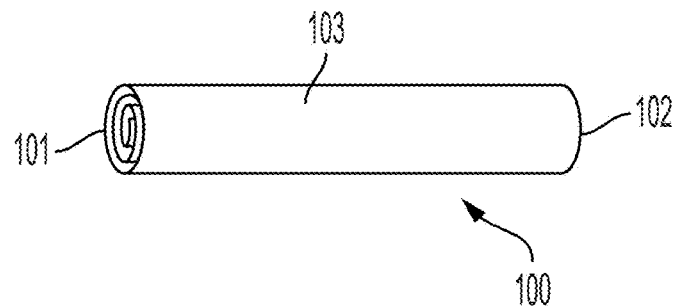
FIG. 1A depicts an exemplary embodiment of the implantable, bioerodible, drug delivery device.
Figure 1B:
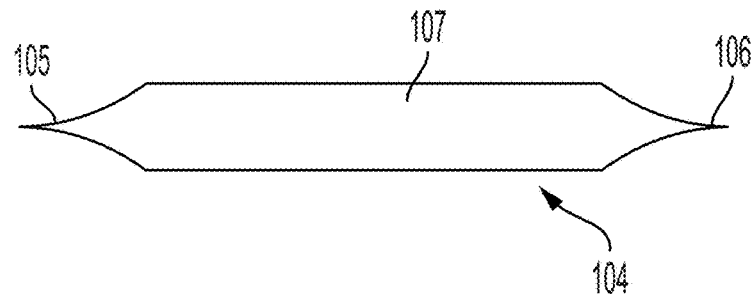
FIG. 1B depicts an exemplary embodiment of the implantable, bioerodible, drug delivery device having tapered ends.
Figure 3:
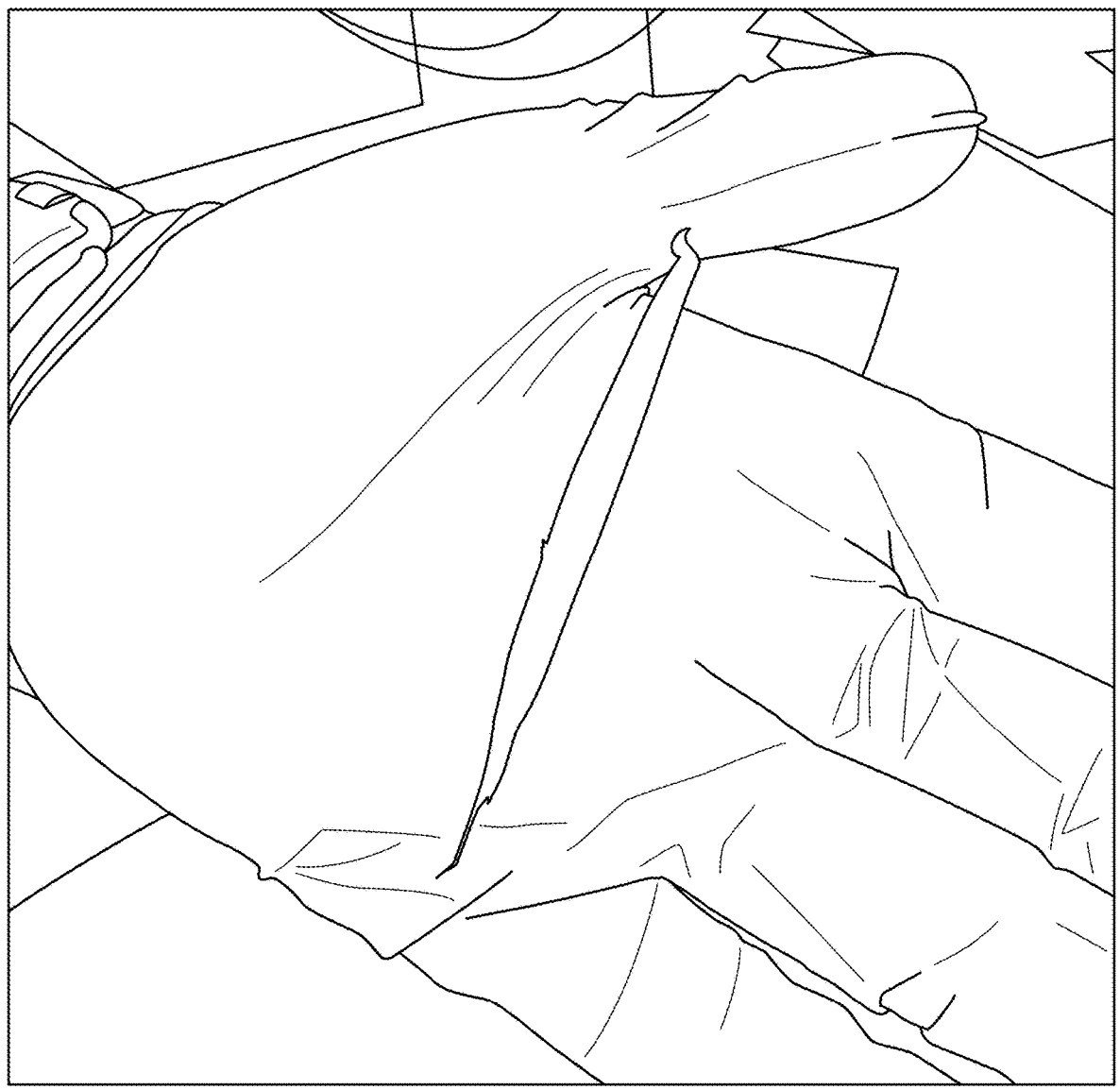
FIG. 3 depicts a photograph of an exemplary embodiment of an implantable, bioerodible, drug delivery device.

Disclosed herein are bioerodible drug delivery devices that include bioerodible fibers and at least one active agent, and related methods. In some embodiments, the device can be in a rolled configuration. As shown in FIG. 1A, exemplary device (100) has a first end (101) and a second end (102), spaced apart from one another and a body portion (103) defined between the first and second ends. In FIG. 1B another exemplary device (104) includes body portion (107) tapering towards first end (105) and second end (106). A photograph of exemplary device (104) is provided in FIG. 3. In further embodiments, one end of the device will be tapered and the other cut in cross section.

Figure 2:
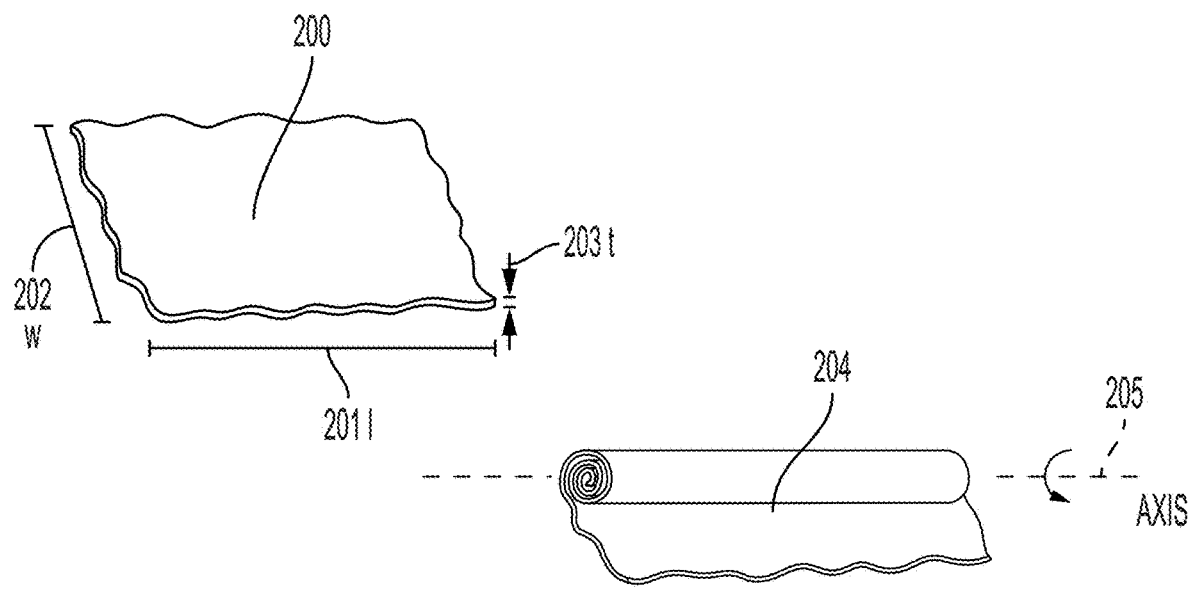
FIG. 2 depicts an exemplary fiber/drug sheet that is unrolled (left) and in partially rolled configuration (right).

In some instances, the device includes a sheet of bioerodible fibers and at least one active agent. The sheet has a length, width, and thickness, and in a rolled configuration comprising multiple turns along an axis that is parallel to the length of the sheet. One embodiment is depicted in FIG. 2, in which a sheet (200) has a length (l) (201), width (w) (202) and thickness (t) (203). The sheet can be rolled about an axis (205) parallel to the length (201) of the sheet (200) to form an implantable device. FIG. 2 also depicts sheet (204) in partially rolled configuration, which may be converted to the implantable device by completely rolling along width (202).

In some embodiments, sheet (200) can have a length (201) from 10-1,000 mm, from 10-750 mm, from 10-500 mm, from 25-500 mm, from 50-500 mm, from 50-400 mm, from 75-400 mm, from 100-350 mm, from 200-350 mm, from 10-250 mm, from 10-200 mm, from 10-150 mm, from 10-100 mm, from 10-75 mm, from 10-50 mm, from 25-100 mm, from 50-100 mm, or from 75-150 mm. Sheet (200) can have a width (202) from 10-10,000 mm, from 10-5,000 mm, from 10-2,500 mm, from 10-2,000 mm, from 10-1,500 mm, from 10-1,000 mm, from 10-750 mm, from 10-500 mm, from 50-500 mm, from 100-500 mm, or from 250-500 mm. In some instances, the sheet (200) can have a length (201) from 10-75 mm and a width (202) from 150-400 mm. The sheet can have a thickness (203) from 50-2,000,000 nm, from 50-1,000,000 nm, 50-500,000 nm, from 50-250,000 nm, 50-100,000 nm, from 50-50,000 nm, 50-25,000 nm, from 50-10,000 nm, from 50-5,000 nm, from 50-2,500 nm, from 50-1,000 nm, from 50-500 nm, from 50-250 nm, from 50-100 nm, from 100-2,000,000 nm, from 100-1,000,000 nm, 100-500,000 nm, from 100-250,000 nm, 100-100,000 nm, from 100-50,000 nm, 100-25,000 nm, from 100-10,000 nm, from 100-5,000 nm, from 100-2,500 nm, from 100-1,000 nm, from 100-500 nm, from 100-250 nm, from 250-2,000,000 nm, from 250-1,000,000 nm, 250-500,000 nm, from 250-250,000 nm, 250-100,000 nm, from 250-50,000 nm, 250-25,000 nm, from 250-10,000 nm, from 250-5,000 nm, from 250-2,500 nm, from 250-1,000 nm, from 250-500 nm, from 500-2,000,000 nm, from 500-1,000,000 nm, 500-500,000 nm, from 500-250,000 nm, 500-100,000 nm, from 500-50,000 nm, 500-25,000 nm, from 500-10,000 nm, from 500-5,000 nm, from 500-2,500 nm, from 500-1,000 nm, from 1,000-2,000,000 nm, from 1,000-1,000,000 nm, 1,000-500,000 nm, from 1,000-250,000 nm, 1,000-100,000 nm, from 1,000-50,000 nm, 1,000-25,000 nm, from 1,000-10,000 nm, from 1,000-5,000 nm, from 1,000-2,500 nm, from 2,500-2,000,000 nm, from 2,500-1,000,000 nm, 2,500-500,000 nm, from 2,500-250,000 nm, 2,500-100,000 nm, from 2,500-50,000 nm, 2,500-25,000 nm, from 2,500-10,000 nm, from 2,500-5,000 nm, from 5,000-2,000,000 nm, from 5,000-1,000,000 nm, 5,000-500,000 nm, from 5,000-250,000 nm, 5,000-100,000 nm, from 5,000-50,000 nm, 5,000-25,000 nm, from 5,000-10,000 nm, from 10,000-2,000,000 nm, from 10,000-1,000,000 nm, 10,000-500,000 nm, from 10,000-250,000 nm, 10,000-100,000 nm, from 10,000-50,000 nm, 10,000-25,000 nm, from 25,000-2,000,000 nm, from 25,000-1,000,000 nm, 25,000-500,000 nm, from 25,000-250,000 nm, 25,000-100,000 nm, from 25,000-50,000 nm, from 50,000-2,000,000 nm, from 50,000-1,000,000 nm, 50,000-500,000 nm, from 50,000-250,000 nm, 50,000-100,000 nm, from 100,000-2,000,000 nm, from 100,000-1,000,000 nm, 100,000-500,000 nm, from 100,000-250,000 nm, from 250,000-2,000,000 nm, from 250,000-1,000,000 nm, 250,000-500,000 nm, from 500,000-2,000,000 nm, from 500,000-1,000,000 nm, or from 1,000,000-2,000,000 nm.

In certain embodiments, for every 50 mm of sheet width, there can be at least 1 turn, at least 2 turns, at least 3 turns, at least 4 turns, at least 2 turns, at least 3 turns, at least 4 turns, at least 5 turns, at least 6 turns, at least 7 turns, at least 8 turns, at least 9 turns, at least 10 turns, at least 15 turns, at least 20 turns, at least 25 turns, or at least 50 turns. In some embodiments, for every 50 mm of sheet width, there can be from 1-50 turns, from 2-50 turns, from 2-25 turns, from 2-15 turns, from 2-10 turns, or from 2-5 turns.

In some embodiments, device (205) has a length (207) from 10-1,000 mm, from 10-750 mm, from 10-500 mm, from 25-500 mm, from 50-500 mm, from 50-400 mm, from 75-400 mm, from 100-350 mm, or from 200-350 mm. Given the nature of the materials involved, the implantable device is not necessarily a perfect cylinder. As used herein, the term "diameter" refers to the longest length for any cross-section taken perpendicular along the length. The implantable devices disclosed herein may have a diameter from 0.1-10 mm, from 0.1-8 mm, from 0.25-8 mm, from 0.5-8 mm, from 1-8 mm, from 1-5 mm, from 1-4 mm, or from 2-5 mm. In one preferred embodiment, the device has a length from about 200-400 mm, and a diameter from about 1-4 mm.

The bioerodible fibers can have an average fiber diameter from 50-10,000 nm, from 100-10,000 nm, from 250-10,000 nm, from 500-10,000 nm, from 1,000-10,000 nm, from 2,500-10,000 nm, from 5,000-10,000 nm, from 50-1,000 nm, from 100-1,000 nm, from 250-1,000 nm, from 500-1,000 nm, from 50-500 nm, from 50-250 nm, or from 50-100 nm.

The devices may further be wrapped with ties or netting to preserve the shape of the device prior to implantation. Bioerodible suture materials, which are well known in the art, may be used for the ties or netting.

The active agent can be dispersed throughout the device. The weight ratio of (a) bioerodible polymer to (b) active agent can be from 100:1 to 1:10. In some instances, the weight ratio of (a) to (b) can be from 50:1 to 1:10, from 50:1 to 1:5, from 50:1 to 1:1, from 25:1 to 1:1, from 10:1 to 1:1, from 8:1 to 1:1, from 6:1 to 1:1, from 5:1 to 1:1, from 4:1 to 1:1, from 3:1 to 1:1, from 2:1 to 1:1, or from 1.5:1 to 1:1.

Devices disclosed herein according to some embodiments are characterized by a consistent release rate of active agent over prolonged periods of time. For instance, after implantation the device can release a therapeutically effective amount of the active agent for a period of at least 3 months, at least 6 months, at least 9 months, at least 12 months, at least 18 months, at least 24 months, at least 30 months, at least 36 months, at least 42 months, at least 48 months, at least 54 months, or at least 60 months. In some instances, the devices disclosed herein will release a therapeutically effective amount of the active agent for a period of 1-60 months, 3-60 months, 1-54 months, 3-54 months, 3-48 months, 6-48 months, 9-48 months, 12-48 months, 12-36 months, 12-24 months, 12-18 months, 18-48 months, 24-48 months, 24-42 months, 30-42 months, 30-60 months, 36-60 months, 42-60 months, or 48-60 months. In other embodiments, the devices disclosed herein will release a therapeutically effective amount of the active agent for a period of 1-52 weeks, 1-48 weeks, 1-44 weeks, 1-40 weeks, 1-36 weeks, 1-30 weeks, 4-52 weeks, 8-52 weeks, 12-52 weeks, 12-44 weeks, 12-36 weeks, or 12-24 weeks.

According to some embodiments described herein, the devices herein permit consistent release of active agent over the therapeutic period defined above. Certain prior drug delivery systems have been characterized by a "burst release," meaning that upon administration there is a rapid rise in drug plasma concentration followed by a rapid drop in plasma concentration. In certain preferred embodiments, the drug release profile the devices disclosed herein does not exhibit such burst kinetics. Rather, after administration, the active agent plasma concentration rises to, but does not substantially exceed, the target plasma concentration. Moreover, the disclosed devices permit a consistent release of active agent over the therapeutic period. For instance, the plasma concentration can vary no more than 50%, 45%, 40%, 35%, 30%, 25%, 20%, 25%, 20%, 15%, 10%, or 5% over the therapeutic period, as described above. In certain preferred embodiments, the plasma concentration varies no more than 25% over a 36-month period, a 30 month period, a 24 month period, an 18 month period, a 16 month period, a 14 month period, or a 12 month period.

The implantable devices can have a controlled degradation rate, depending on the bioerodible polymer and density of the device (i.e., the number of turns for a sheet length). The device can degrade at a rate of no more than 1.0% mass per day, no more than 0.75% mass per day, no more than 0.5% mass per day, no more than 0.25% mass per day, no more than 0.20% mass per day, no more than 0.15% mass per day, no more than 0.10% mass per day, or no more than 0.05% mass per day. In certain embodiments, the device will undergo a faster degradation in the immediate period following implantation. In such embodiments, after twenty weeks following implantation, the mass of the device will decrease by 3-30%, 3-25%, 3-20%, 3-15%, 3-10%, 5-10%, or 7.5-15%. The remainder of the device will degrade over the therapeutic period, as defined above.

In some preferred embodiments, the non-woven sheet includes an electrospun bioerodible polymer. In some embodiments, the bioerodible polymer is sufficiently hydrophobic to control the release of the active agent. The bioerodible polymer can have a contact angle greater than about 90°, greater than about 100°, greater than about 110°, greater than about 1200 greater than about 130°, greater than about 1400 greater than about 150°, or greater than about 160°. In some embodiments, the bioerodible polymer can have a contact angle between about 90-150°, between about 100-150°, between about 110-150°, between about 120-150°, or between about 125-150°.

Suitable polymers include polyesters, polycarbonates, polyanhydrides, polyamides, polyurethanes, polyketals, polyacetals, polydioxanones, polyesteramides, polyorthoesters, polyorthocarbonates, polyphosphazenes, polypeptides, polyvinyls, polyalkylene oxides, polysaccharides, copolymers thereof, and combinations thereof. Exemplary polymers include poly(caprolactone), poly(glycolic acid), poly(lactic acid), poly(hydroxybutryate); poly(maleic anhydride); poly(malic acid), poly(ethylene glycol), poly(vinylpyrrolidone), poly(methyl vinylether), hydroxycellulose; chitin; chitosan; alginate, hyaluronic acid, and copolymers thereof. Combinations of the aforementioned polymers may also be employed.

In some preferred embodiments, the implantable device includes one or more poly(lactic acid) polymers, such as poly(L-lactic acid), poly(D-lactic acid), poly(D/L-lactic acid), copolymers thereof, and combinations thereof. The molecular weight of the poly(lactic acid) can be from 10,000-2,500,000 g/mol, from 50,000-2,500,000 g/mol, from 100,000-2,500,000 g/mol, from 250,000-2,500,000 g/mol, from 100,000-2,000,000 g/mol, from 100,000-1,500,000 g/mol, from 100,000-1,000,000 g/mol, from 250,000-1,000,000 g/mol, from 500,000-1,000,000 g/mol, or from 250,000-900,000 g/mol, In some embodiments the bioerodible polymer can include one or more of poly(lactic-co-glycolic) acid ("PLGA"), polycaprolactone, polyglycolide, polyhydroxybutyric acid, poly(sebacic acid), poly[1,6-bis(p-carboxyphenoxy)hexane], and mixtures thereof. In certain cases, polycaprolactone can be used in combination with other polymeric systems. Suitable other systems include poly (ethylene glycols) ("PEG"), and PEG copolymers. Exemplary copolymers include polycaprolactone-poly(ethylene glycol).

The types of active agents that can be delivered using the implantable devices disclosed herein is not particularly limited. In preferred embodiments, the active agent is a drug that is regularly administered over a period of weeks, months, or years. Suitable agents include analgesic agents; anti-anxiety agents; anti-arthritic agents; anti-asthmatic agents; anticancer agents; anticholinergic agents; anticholinesterases; anticonvulsants; antidepressants; an antidiabetic agents; antidiarrheal agents; anti-emetic agents; antihistamines; antihyperlipidemic agents; anti-infective agents; anti-inflammatory agents; antimigraine agents; anti-obesity agents; antipruritic agents; antipsychotic agents; antispasmodic agents; neurological agents; cardiovascular medicaments; diuretic agents; gastrointestinal medications; hormones; anti-hormones; hypnotic agents; immunosuppressive agents; leukotriene inhibitors; narcotic agonists, narcotic antagonists; neurotransmitters; nicotine; nucleic acids; peptide drugs; thrombolytic agents; vasodilators; or a combination thereof Some preferred active agents include contraceptive drugs. For instance, the active agent can be a progestogen such as 21-acetoxypregnenolone; allylestrenol; anagestone (17α-hydroxy-6α-methylpregn-4-en-20-one); anagestone 17α-acetate; chlormadinone; chlormadinone 17α-acetate; chloroethynyl norgestrel; cyproterone; cyproterone 17α-acetate; desogestrel; dienogest; dimethisterone (6α,21-dimethylethisterone); drospirenone (1,2-dihydrospirorenone); ethisterone (17α-ethinyltestosterone or pregneninolone); ethynerone; etynodiol diacetate (norethindrol diacetate); etonogestrel (11-methylene-levo-norgestrel; 3-keto-desogestrel); gestodene; hydroxyprogesterone (17α-hydroxyprogesterone); hydroxyprogesterone caproate; hydroxyprogesterone acetate; hydroxyprogesterone heptanoate; levonorgestrel; lynestrenol; medrogestone (6,17α-dimethyl-6-dehydroprogesterone); medroxyprogesterone; medroxyprogesterone acetate; megestrol; megestrol acetate; segesterone acetate; nomegestrol; nomegestrol acetate; norethindrone (norethisterone; 19-nor-17α-ethynyltestosterone); norelgestromin (17-deacetylnorgestimate); noretynodrel; norgestrienone; progesterone; and retroprogesterone. In certain embodiments, combinations of progestogen can be delivered. One preferred contraceptive agent is etonogestrel.

In some instances, the active agent can be an estrogenic compound. Suitable estrogenic compounds include estradiol, estradiol esters, including estradiol benzoate, valerate, cypionate, heptanoate, decanoate, acetate and diacetate; 17α-estradiol; ethinylestradiol, ethinylestradiol esters (e.g., ethinylestradiol 3-acetate and ethinylestradiol 3-benzoate); estriol; estriol succinate; polyestrol phosphate; estrone, estrone esters (e.g., estrone acetate, estrone sulfate, and piperazine estrone sulfate); quinestrol; mestranol; conjugated equine estrogens, and combinations thereof.

In some cases, one or more hormone and hormone therapeutics can be administered using the disclosed devices. Exemplary such agents include gonadotropin-releasing hormone.

In some instances, the active agent includes an anti-addiction drug. Such agents can reduce the cravings or euphoria associated with addictive substances such as narcotics or alcohol. Some agents, like diulfiram, can also induce substantial discomfort when the patient takes the addictive substance. However, in the case of orally administered anti-addiction agents, patient compliance can be an issue. Compliance issues may be overcome using the implantable devices disclosed herein in accordance with some embodiments. For such embodiments, the active agent can include one or more anti-addiction drugs like disulfiram, coprine, acamprosate, calcium carbamide, lofexidine, methadone, buprenorphine, or naltrexone.

In other embodiments, the active agent includes a CNS therapeutic agent, for instance an anti-psychotic such as paliperiodone, risperidone, lurasidone, lloperidone, ziprasidone, aripiprazole, brexipiprazole, caripazine, asenapine, clozapine, olanzapine, quetiapine, zotepine, blonanserin, pimavanserin, sertindole, phenothiazines, thioxanthenes, butyrophenones such as benpridol, bromperidol, droperidol, haloperidol, and timiperone. The active agent can be a cholinesterase inhibitor such as physostigmine, neostigmine, pyridostigmine, ambenonium, demecarium, rivastigmine, galantamine, and donepezil. Other suitable CNS agents include memantine and ergot alkaloids.

In other embodiments, the active agent includes one or more veterinary drugs, for instance antiparasitics, antiprotozoals, antibiotics, insecticides, anthelmintics, antifungals, anti-inflammatorys, antirheumatics, steroids, and combination thereof.

The devices according to some embodiments disclosed herein may include at least one radiopaque material. Such materials can be useful for guiding both the implantation of the device, as well as its removal, should such a need arise ahead of its complete degradation. Exemplary radiopaque materials include elements such as barium, bismuth, titanium, iodine, or tungsten, and compounds including barium sulfate, titanium oxide, bismuth trioxide, benzene triiodide, and tungsten metal may be mentioned as suitable radiopaque materials. The radiopaque material may be included in the device in an amount from 2-25%, from 5-25%, from 5-20%, from 5-15%, or from 5-10% by weight.

The implantable drug delivery devices may be prepared using electrospinning techniques to produce non-woven fibers from a mixture of bioerodible polymer, active agent, solvent and other optional components as described herein.

Suitable electrospinning techniques include conventional needle electrospinning and free surface electrospinning. Free surface electrospinning includes needle-less and bubble electrospinning. Exemplary free surface electrospinning techniques are disclosed in U.S. Pat. No. 9,903,050, the contents of which are hereby incorporated in its entirety.

In needle electrospinning, a solution including bioerodible polymer and active agent is fed through one or more needles charged to high electrical potential relative to a grounded collector. Because of injected charges that accumulate on the elongated solution front at the needle, repulsive electrical forces overwhelm surface tension and stretch the jet as it accelerates toward the electrical ground. Due to the interaction between the jet and external electric field and charge repulsion inside the jet, the charged jet undergoes whipping instability to further stretch it thinner. In the meantime, the solvent evaporates and the entanglements of the polymer chains prevent the jet from breaking up, resulting in fine fibers which are deposited as random nonwoven mat on the collector.

The one or more needles can have a gauge from 10-34, from 15-34, from 15-30, from 20-30, or from 25-30. In some embodiments, the needle can have a gauge of at least 10, at least 15, at least 20, at least 25, or at least 30. The solution can be passed through the needle at a rate of 0.005-0.5 ml/hr, 0.01-0.25 ml/hr, 0.01-0.1 ml/hr, 0.025-0.1 ml/hr, or 0.025-0.075 ml/hr.

In an exemplary method of free surface electrospinning, an electric voltage is applied to a wire electrode, which is drawn through a solution including bioerodible polymer and active agent. As the electrode is removed from the solution, the solution coating the film experiences Plateau-Rayleigh instability, causing beads of solution to form upon the electrode. In the presence of an electric field, the beads deform into Taylor cones, and then jet towards an adjacent grounded collector as described above with conventional needle electrospinning.

The wire electrode can have a radius from 10-1,000 μm, from 25-1,000 μm, from 100-1,000 μm, from 250-1,000 μm, from 500-1,000 μm, 10-500 μm, from 25-500 μm, from 100-500 μm, from 250-500 μm, from 10-250 μm, from 25-250 μm, from 50-250 μm, or from 100-250 μm.

The wire electrode can be mounted on a spindle which rotates the wire electrode in and out of the solution. The rotation frequency can be from 1-50 rpm, from 1-40 rpm, from 1-30 rpm, 1-25 rpm, from 1-20 rpm, from 1-15 rpm, from 1-10 rpm, from 1-5 rpm, 2-25 rpm, from 2-20 rpm, from 2-15 rpm, from 2-10 rpm, from 2-5 rpm, 5-25 rpm, from 5-20 rpm, from 5-15 rpm, from 5-10 rpm, from 5-15 rpm, or from 10-15 rpm. In some instances, multiple electrodes can be mounted on the same spindle.

The applied voltage for the above described electrospinning processes can be from 1-100 kV, from about 2-50 kV, from about 5-50 kV, from about 10-50 kV, from about 10-30 kV, from about 15-30 kV, or from about 20-30 kV.

The grounded collector is spaced apart the location where the Taylor cone is generated. For instance, the distance between the generated Taylor cone and grounded collector can be from 1-100 cm, from 1-50 cm, from 5-50 cm, from 5-75 cm, from 10-50 cm, from 10-75 cm, from 20-40 cm, or from 25-35 cm.

In some embodiments, the collector is a flat plate. In some embodiments, the flat plate is stationary, while in other embodiments the flat plate is shifted during the electrospinning process along an axis perpendicular to the flow of material between the Taylor cone and collecting surface to provide a continuous electrospinning process. In further embodiments, the collector is a rotating drum, which permits the continuous harvesting of electrospun sheets. In yet further embodiments, the collector is a rotating mandrel. In this embodiment, the implantable drug delivery device having a rolled configuration can be directly obtained from an electrospinning process. The mandrel can have a radius from 10-10,000 μm, from 50-10,000 μm, 100-10,000 μm, from 250-10,000 μm, from 500-10,000 μm, from 1,000-10,000 μm, from 100-5,000 μm, from 500-5,000 μm, from 500-2,500 μm, from 10,000-100,000 μm, from 25,000-100,000 μm, from 50,000-100,000 μm, from 10,000-500,000 μm, from 100,000-500,000 μm, or from 250,000-500,000 μm. The mandrel can be rotated at a rate from 10-5,000 rpm, from 10-2,500 rpm, from 10-1,000 rpm, from 50-1,000 rpm, from 100-1,000 rpm, from 100-500 rpm, or from 500-1,000.

Suitable solvents include aprotic solvents like dimethylsulfoxide (DMSO), halogenated hydrocarbons like chloroform and methylene chloride, ethers like tetrahydrofuran (THF) and diethylether, carbonyl- or nitrile-containing compounds like dimethylformamide (DMF), acetone, acetonitrile, ethyl acetate, methylethylketone, and the like. Suitable solvents can also include protic solvents such as water, organic acids like formic acid, acetic acid, propionic acid, trichloroacetic acid, chloroacetic acid, trifluoroacetic acid and the like, or alcohols like methanol, ethanol, ethylene glycol, glycerol, isopropanol, and n-propanol. In some embodiments, the solvent can be a mixture of two solvents, for instance a halogenated hydrocarbon and a carbonyl-containing solvent.

The weight ratio of bioerodible polymer to active agent can be from 5:1 to 1:5, 2.5:1 to 1:2.5, 2.5:1 to 1:1, 2:1 to 1:1, or 1.5:1 to 1:1. The concentration of bioerodible polymer in the solution can be from 0.01-1,000 mg/ml, from 0.1-1,000 mg/ml, 1-1,000 mg/ml, from 0.1-500 mg/ml, from 0.1-250 mg/ml, from 0.1-100 mg/ml, from 0.1-50 mg/ml, from 1-100 mg/ml, from 1-50 mg/ml, from 5-50 mg/ml, from 10-50 mg/ml, or from 15-25 mg/ml.

In those embodiments including a radiopaque material, the radiopaque material may be included in the solution for electrospinning.

For embodiments employing a flat or drum collector, the resulting mat may be converted into the drug device by rolling the mat along an axis. In some embodiments, the mat may be cut the desired length and width and then rolled, while in other embodiments, the mat may be rolled, and then cut into the desired shape.

The devices disclosed herein may be implanted subcutaneously into various locations in the subject, for instance in the upper arm, thigh or torso. In other embodiments, the device may be implanted intravaginally, intravascularly, intraocular, intrathecal, and peritoneal. The devices may also be employed for site-selective drug delivery, for instance in cardiac and brain tissues. In other cases, the device may be implanted directly into or adjacent a tumor or infection site.

The devices disclosed herein may be used to treat or prevent a wide variety of medical conditions. For instance, the devices may be used to treat neurological disorders such as Alzheimer's disease, Huntington's disease, Parkinson's disease, multiple sclerosis, narcolepsy, epilepsy, tics, paralysis, tremors, and dementia. In other embodiments, the devices may be used to treat conditions like precocious puberty. In yet further embodiments, the devices disclosed herein may be used to treat cancer. The skilled person is capable of selecting the appropriate chemotherapeutic agent to treat the particular cancer. In other embodiments, the devices can be used to treat addition and prevent relapse in recovering addicts.

In one preferred embodiment, devices disclosed herein can be used for preventing pregnancy in a mammal. The devices can be loaded with one or more contraceptive agents, as defined above, and implanted into the target subject.

If it is desired to remove the device prior to complete agent release and degradation, the device may be extracted using conventional surgical techniques, aided by radiopaque materials as described above. In some embodiments, the degradation of the device may be acceleration by altering the local pH around the device by injection of an appropriate acid or base solution.

EXAMPLES

The following examples are for the purpose of illustration of the certain aspects and embodiments of the present invention only and are not intended to limit the scope of the present invention in any manner whatsoever.

0.140 g PLLA is mixed with 4.8 mL chloroform in a 20 mL scintillation vial using a vortexer. Once the PLLA is dissolved and no more visible solids can be seen in the vial, 1.2 mL of acetone is added to the vial and mixed on the vortexer for 2 minutes. 100 mg of etongestrel is then added to the vial and mixed using the vortexer. The resulting solution should be viscous but not too thick. The solution is drawn into a syringe, and set in a linear actuator and tubing leading to the needle fastened on the metal plate connected to a battery set to 23.7 kV. A collector plate covered in aluminum foil is set 25-35 cm from the needle tip. The solution is forced through the needle at a rate of 0.06 ml/hr, and the resulting fibers are collected on the plate. The fibers are separated from the plate and rolled to give the implantable device.

The devices and methods of the appended claims are not limited in scope by the specific compositions and methods described herein, which are intended as illustrations of a few aspects of the claims and any devices and methods that are functionally equivalent are intended to fall within the scope of the claims. Various modifications of the devices and methods in addition to those shown and described herein are intended to fall within the scope of the appended claims. Further, while only certain representative devices and method steps disclosed herein are specifically described, other combinations of the devices and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A bioerodible drug delivery device comprising a non-woven sheet having a length, width and thickness, said non-woven sheet in a rolled configuration comprising multiple turns along an axis parallel to the sheet length and perpendicular to the sheet width,
   wherein the non-woven sheet comprises an electrospun bioerodible polymer and at least one active agent,
   wherein the non-woven sheet is electrospun from a solution comprising the bioerodible polymer at a concentration from 25-50 mg/ml,
   wherein the solution comprises the bioerodible polymer and active agent at a weight ratio from 2.5:1 to 1:2.5,
   wherein the bioerodible polymer is poly(L-lactic acid),
   wherein the active agent is etonogestrel,
   wherein the non-woven sheet has a length from about 25-75 mm and the device has a diameter from about 2-4 mm, and
   wherein after implantation of the device into a patient, a therapeutic amount of the active agent is released for a period of at least 18 months.

2. The device according to claim 1, wherein the non-woven sheet has a width of 20-500 mm and comprises at least 2 turns per 50 mm of width.

3. A method for preparing the device according to claim 1, comprising:

(a) applying an electric voltage from a voltage source to a solution to form a charged solution,
(b) forming at least one drop of the charged solution by passing the charged solution through a needle at a rate of 0.05-0.5 ml/hr,
(c) forming an electrospun non-woven sheet on a grounded collector spaced apart from the drop along a first axis, and
(d) converting the non-woven sheet to a rolled configuration comprising multiple turns along an axis parallel to the sheet length and perpendicular to the sheet width,
wherein the charged solution comprises etonogestrel and poly(L-lactic acid),
wherein the grounded collector is a flat surface or a rotating rod,
wherein the concentration of poly(L-lactic acid) in the charge solution is from 25-50 mg/mL,
wherein the charged solution contains poly(L-lactic acid) and etonogestrel at a weight ratio from 2.5:1 to 1:2.5,
wherein the non-woven sheet has a length from about 25-75 mm and the device has a diameter from about 2-4 mm, and
wherein after implantation of the device into a patient, a therapeutic amount of the active agent is released for a period of at least 18 months.

* * * * *